United States Patent [19]

Williams

[11] 4,418,201
[45] Nov. 29, 1983

[54] PROCESS FOR PREPARATION OF N-HETEROCYCLIC COMPOUNDS

[75] Inventor: Billy M. Williams, Midland, Mich.
[73] Assignee: The Dow Chemical Company, Midland, Mich.
[21] Appl. No.: 150,500
[22] Filed: May 16, 1980
[51] Int. Cl.³ .................................................. C07D 207/06
[52] U.S. Cl. .............................. 548/579; 260/239 A; 260/239 E; 546/184; 546/192; 546/216; 546/217; 546/219; 546/242; 548/542; 548/544; 548/545; 548/577
[58] Field of Search ............... 546/184, 217, 219, 192, 546/242, 216; 260/326.8, 326.5 R, 239 E, 239 AR; 548/542, 544, 545, 577, 579

[56] References Cited

U.S. PATENT DOCUMENTS

| 2,863,872 | 12/1958 | Silverstone | 546/184 |
| 3,029,240 | 4/1962 | Erner | 544/404 |
| 3,691,197 | 9/1972 | Brown et al. | 260/326.8 |
| 3,903,079 | 9/1975 | Heinz et al. | 546/184 X |
| 4,001,213 | 1/1977 | Hershman et al. | 546/184 X |

OTHER PUBLICATIONS

Olah, G. (Editor), *Friedel-Crafts and Related Reactions*, vol. I, Interscience, New York, 1963, pp. 296-298 and 329.
Stavrovskaya, V., *J. Gen. Chem.* (USSR), 25, 133-134 (1955).

*Primary Examiner*—Richard A. Schwartz
*Attorney, Agent, or Firm*—Douglas N. Deline

[57] ABSTRACT

Nitrogen-containing heterocyclic compounds are prepared by the Lewis acid catalyzed cyclization of a diamino-substituted aliphatic compound of the formula $$R_2N-(CR'_2)_{x+1}-NR''_2$$

wherein R, R' and R" are specified substituents and x is an integer from 1 to 4.

10 Claims, No Drawings

PROCESS FOR PREPARATION OF N-HETEROCYCLIC COMPOUNDS

BACKGROUND OF THE INVENTION

Several researchers have reported the successful cyclization of various aliphatic diamines to produce the corresponding heterocyclic imine compounds. In U.S. Pat. No. 2,952,688 a process for converting tetramethylene diamine to pyrrolidine using a supported nickel catalyst is disclosed. The compound is merely heated to a temperature of 100° C.-160° C. in the presence of the catalyst. Ammonia is liberated during the course of the reaction.

Later researchers have favored the use of vapor phase processes in order to avoid formation of oligomeric or polymeric by-products. For example, in U.S. Pat. No. 3,903,079 and U.S. Pat. No. 4,001,213, dehydrated crystalline aluminosilicate molecular sieve catalysts and metal or metal oxide catalysts respectively are disclosed. In the later reference nitrogen or hydrogen diluent gases are also employed in order to avoid polymeric by-products.

It has now surprisingly been found that relatively pure heterocyclic compounds may be prepared according to the instant invention by means of a liquid phase cyclization of aliphatic diamines without concomitant formation of polymeric by-products are predicted by prior art references. The ability to operate utilizing ordinary reaction containers and without the need for complex process equipment is considered an additional advantage.

SUMMARY OF THE INVENTION

The invented process involves the Lewis acid catalyzed liquid phase cyclization of a diamino-substituted aliphatic compound of the formula

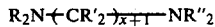

$$R_2N\text{---}(CR'_2)_{x+1}\text{---}NR''_2$$

where R, R' and R" independently each occurrence are selected from hydrogen, phenyl and $C_{1-20}$ alkyl, alkoxy or polyalkoxy; and x is an integer from 1 to 4.

The products formed are a corresponding saturated heterocyclic compound of the formula

$$CR'_2\text{---}(CR'_2)_x\text{---}NR$$

and a co-product amine of the formula $RNR''_2$, wherein R, R', R" and x have the same definitions as above.

Preferably, R" in each occurrence is $C_{1-4}$ alkyl and R in each occurrence is hydrogen, i.e., one amino moiety is primary, the other is tertiary. The intermediate formed from such a tertiary amino moiety during the reaction is more stable than is the corresponding intermediate species from a primary amino moiety. Consequently elimination of the tertiary amino moiety is favored thus producing the corresponding desired N-heterocyclic compound and a dialkyl amine. Most preferred reactants are compounds of the above formula wherein additionally R' is, in at least one occurrence, $C_{1-4}$ alkyl and x is 3, e.g., 2-amino-5-dialkylaminopentane, 2-amino-5-dialkylaminohexane, 1-amino-2,3-dibutyl-4-dialkylaminobutane, etc. Such compounds are most desirable intermediates for further synthesis of pharmaceutical compounds.

Suitable catalysts according to the invented process are the Lewis acids, for example, $FeCl_3$, $AlCl_3$, $I_2$, $ZnCl_2$, $TiCl_4$, $PCl_5$, $FeI_2$, etc. Preferred catalysts are $FeCl_3$, $AlCl_3$ and $I_2$.

DETAILED DESCRIPTION OF THE INVENTION

The reaction is performed by heating the diamino-substituted reactant in the presence of the Lewis acid catalyst to a temperature at which the cyclization reaction takes place, generally about 100° C. to about 200° C., preferably about 150° C.-190° C. A short induction period may be required depending on the particular catalyst. Reaction is continued for several hours or more and may of course be discontinued at any time depending on the desired degree of completion of the reaction.

In the preferred operating procedure the diamino-substituted reactant remains a liquid under the reaction conditions. In the event the normal boiling point of the diamine is less than the reaction temperature, pressure is advantageously employed. Alternatively, the reactant may be combined with a high boiling inert solvent such as an alkyl monoether or diether of a (poly)alkyleneglycol. The latter method is not preferred however, since lowered yields have been observed when reactant physical properties required the utilization of a solvent.

Employing the most preferred diamino-substituted reactants, the products and coproducts formed are an alkyl-substituted pyrrolidine compound and the co-product dialkyl amine which may be collected as they are distilled from the reaction. The generally large difference in boiling points allows the product and coproduct to be easily separated by a second fractional distillation.

In the event the product and coproduct formed are not sufficiently lower boiling than the initial reactant it will be necessary to fractionate the three components of the resulting mixture or perhaps employ additional means of separation such as liquid chromatography. Similar techniques of separation well-known in the art may be used when a solvent is employed.

The catalysts of the invention are employed in a catalytically effective amount. Preferably amounts from 0.01 percent to 10 percent by weight based on the diamine reactant, and most preferably from about 0.5 to about 5 percent are employed. Because the catalysts are not degraded during the reaction they may easily be recycled for reuse in subsequent reactions.

Other by-products formed during the reaction are primarily the corresponding pyrrolidine formed by removal of the alternate amino group. By use of the preferred reactant containing one primary and one tertiary amine it is possible to limit formation of N,N-dialkyl-substituted pyrrolidone to amounts of 5 percent or less. Operation according to the most preferred operating conditions results in formation of the desired alkyl-substituted N-heterocyclic compound in high yield and purity, without the formation of large amounts of undesirable by-products including polymers.

The products formed are widely used in the manufacture of pharmaceutical and other biological chemicals and in other industrial processes.

SPECIFIC EMBODIMENTS

The following examples are provided as further illustrative of the present invention and are not to be construed as limiting.

EXAMPLE 1

Preparation of 2-Methylpyrrolidine

A 5-liter glass flask equipped with a thermometer, magnetic stirrer, heating mantle, condensor, and collecting pot was charged with 2-amino-5-diethylaminopentane (1.2 kg, 7.3 mole). The catalyst, $I_2$ (24.0 g, 2.0 percent) was added and the mixture heated with constant stirring to 180° C.±2° C. The reaction initiated after a very short induction period and the volatile products, diethylamine (b.p. 55° C.) and 2-methylpyrrolidine (b.p. 94° C.), were collected as they distilled overhead.

The reaction was continued for 23 hours. A total of 1045 g of crude reaction product was obtained. Upon fractional distillation using a 12″ Oldershaw column, two fractions were obtained. One collected at a head temperature of 50° C.-65° C. was identified as diethylamine. The fraction collected at a head temperature of 80° C.-94° C. was identified as 2-methylpyrrolidine, of 98 percent purity with the major impurity being N-ethyl-2-methylpyrrolidine. Overall yield of the reaction is about 70–80 percent with about an 80–85 percent conversion of starting reactant.

The remaining component of the crude product was primarily starting material which was recycled and reacted again along with an additional quantity of 2-amino-5-diethylaminopentane. The initial charge of catalyst remaining in the reaction vessel was also reused in subsequent reactions with no adverse effects on product yield or purity observed. Observation after several recycles of catalyst and unreacted reactant indicated polymer formation was practically non-existent.

EXAMPLE 2

The reaction conditions of Example 1 were repeated utilizing various other Lewis acids as catalysts. The results of these reactions are contained in Table I.

TABLE I

| Catalyst | Induction Period (hrs) | Crude Yield % | By-product Level % |
|---|---|---|---|
| $I_2$ | none | 80 | 2–4 |
| $FeCl_3$ | ~3 | 75 | <1.0 |
| $AlCl_3$ | ~4 | 75 | 3–5 |

What is claimed is:

1. A liquid phase process for forming saturated heterocyclic compounds of the formula $$CR'_2-(CR'_2)_x-NR$$

wherein R and R' independently in each occurrence are selected from the group consisting of hydrogen, phenyl and $C_{1-20}$ alkyl, alkoxy or polyalkoxy, and x is an integer from 1 to 4 comprising heating a diamino-substituted aliphatic compound of the formula $$R_2N-(CR'_2)_{x+1}-NR''_2$$

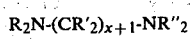

wherein R, R' and x are as above-defined and R″ is selected from the group consisting of hydrogen, phenyl and $C_{1-20}$ alkyl, alkoxy or polyalkoxy in the presence of a catalytically effective amount of a halide-containing Lewis acid at a temperature sufficient to cause formation of the saturated heterocyclic reaction product.

2. The process of claim 1 wherein the diamino-substituted aliphatic compound has a normal boiling point above the temperature employed in the reaction process.

3. The process according to claim 1 wherein the temperature of the reaction is from about 100° C. to about 200° C.

4. The process of claim 1 wherein R″ in each occurrence is $C_{1-4}$ alkyl and R in each occurrence is hydrogen.

5. The process according to claim 4 wherein R' is at least one occurrence is $C_{1-4}$ alkyl and x is 3.

6. The process according to claim 5 wherein the diamino-substituted aliphatic compound is 2-amino-5-diethylaminopentane.

7. The process according to claim 1 wherein the catalyst is selected from $FeCl_3$, $AlCl_3$, $I_2$, $ZnCl_2$, $TiCl_4$, $PCl_5$ and $FeI_2$.

8. The process according to claim 7 wherein the catalyst is selected from $FeCl_3$, $AlCl_3$ and $I_2$.

9. The process of claim 7 or 8 wherein the catalyst is present in a catalytically effective amount from 0.01 percent to 10 percent by weight based on the diamino-substituted aliphatic compound.

10. The process of claim 9 wherein the catalyst is present in a catalytically effective amount from about 0.5 percent to 5.0 percent by weight based on the diamino-substituted aliphatic compound.

* * * * *

UNITED STATES PATENT AND TRADEMARK OFFICE
CERTIFICATE OF CORRECTION

PATENT NO. : 4,418,201

DATED : November 29, 1983

INVENTOR(S) : Billy M. Williams

It is certified that error appears in the above—identified patent and that said Letters Patent is hereby corrected as shown below:

Column 1, line 29, "by-products are predicted" should read -- by-products as predicted --.

Column 1, line 49, formula "$CR'_2-(CR'_2)_x-NR$" should read -- $CR'_2-(CR'_2)_x-NR$ --.

Column 2, line 60, "pyrrolidone to" should read -- pyrrolidine to --.

Column 4, line 12, formula "$CR'_2-(CR'_2)_x-NR$" should read -- $CR'_2-(CR'_2)_x-NR$ --.

Column 4, line 39, "wherein R' is at" should read -- wherein R' in at --.

Signed and Sealed this

Twenty-seventh Day of March 1984

[SEAL]

Attest:

GERALD J. MOSSINGHOFF

Attesting Officer     Commissioner of Patents and Trademarks